US00RE36068E

United States Patent [19]

Kligman

[11] E Patent Number: Re. 36,068

[45] Reissued Date of Patent: Jan. 26, 1999

[54] METHODS FOR TREATMENT OF SUNDAMAGED HUMAN SKIN WITH RETINOIDS

[76] Inventor: Albert M. Kligman, 238 Oceana Dr., Harvey Cedars, N.J. 08008

[21] Appl. No.: 630,872

[22] Filed: Apr. 2, 1996

Related U.S. Patent Documents

Reissue of:

[64] Patent No.: 4,877,805
Issued: Oct. 31, 1989
Appl. No.: 205,057
Filed: Jun. 3, 1988

U.S. Applications:

[63] Continuation of Ser. No. 886,596, Jul. 16, 1986, abandoned, which is a continuation-in-part of Ser. No. 759,505, Jul. 26, 1985, Pat. No. 4,603,146, which is a continuation of Ser. No. 610,711, May 16, 1984, abandoned, which is a continuation-in-part of Ser. No. 297,388, Aug. 28, 1981, abandoned.

[51] Int. Cl.[6] ..... A61K 31/20

[52] U.S. Cl. ..... 514/381; 514/438; 514/532; 514/559; 514/617; 514/622; 514/725

[58] Field of Search ..... 514/381, 438, 514/532, 559, 617, 622, 725

[56] References Cited

U.S. PATENT DOCUMENTS

| | | | |
|---|---|---|---|
| 3,729,568 | 4/1973 | Marks | 514/559 |
| 3,856,934 | 12/1974 | Felty | 424/62 |
| 3,906,108 | 9/1975 | Felty . | |
| 4,247,547 | 1/1981 | Marks | 514/559 |
| 4,396,553 | 8/1983 | Klaus | 560/456 |
| 4,603,146 | 7/1986 | Kligman | 514/559 |
| 4,877,805 | 10/1989 | Kligman | 514/381 |
| 4,888,342 | 12/1989 | Kligman | 514/419 |

OTHER PUBLICATIONS

See Attachment—Part I, Listing of Infomration from Kligman and Bryce File Histories (3 pages).
See Attachment—Part II, Record of Interference No. 102, 638 (22 pages).
U.S. Ser. No. 297,388 (Abandoned).
Thomas et al., *Journal of American Academy of Dermatology* (May 1981), vol. 4, No. 5, pp. 505–513.
U.K. 906,000, Sep. 1962.
U.S. Serial No. 610,711 (Abandoned).
Kligman et al., *Archives of Dermatology* (Oct., 1971), vol. 104, pp. 420 and 421.
Kligman et al., *Archives of Dermatology* (Jan., 1975), vol. 111, pp. 40–48.
Robinson et al., *British Journal of Dermatology* (1975), vol. 92, pp. 703–706.
Kligman et al., *Journal of Investigative Dermatology* (1979), vol. 73, pp. 354–358.
U.S. Ser. No. 759,505 (Issued as the '146 Patent).
U.S. 4,603,146, Jul. 1986, 514/559.
U.S. Ser. No. 886,595 (Abandoned).
U.K. 1,466,062, Mar. 1977.
FR 1,297,730 May, 1972.
Pawson et al., *Journal of Medicinal Chemistry* (1982), vol. 25, pp. 1269–1277.
Saurat (editor), *Symposium Publication—Karger Publishing Company* (1985) ("Retinoids: New Trends in Research and Therapy").
Pawson (Deluca et al. editors), *Annals of the New York Academy of Sciences* (1981), vol. 359, pp. 1–13.
UK 1,335,867, Oct. 1973.
Sporn et al., *1985 Retinoids, Differentiation and Disease*, vol. 113, pp. 1–5.
Elias et al. (editors), *Topical Retinoids: An Update—Proceedings of a Symposium held Apr. 19–20, 1986*, pp. 748–156.
Bollag (Saurat editor), *Retinoids: New Trends in Research and Therapy* (1985), pp. 274–288.
Sporn et al. (editors), *The Retinoids* (1984), vol. 1, pp. 393–413; Newton et al., *Cancer Research* (1980), vol. 40, pp. 3413–3425.
Loeliger et al., *European Journal of Medicinal Chemistry—Chimica Therapeutica* (Jan.–Feb. 1980), vol. 15, No. 1, pp. 9–15.
U.S. Ser. No. 228,212 (issued as the '342 Patent): [no additional art cited].
U.S. Ser. No. 205,057 (issued as the '805 Patent).
Saline, *Philadelphia Magazine* (1980), pp. 102–133.
*Industry Happenings, Drug & Cosmetic, Industries* (1985), p. 86.
UK 1,239,965, Jul. 1981.
FR 2,405,068 Oct. 1977.
German 2,240,187 Feb. 1974.
BE 877,713 Nov. 1979.
Mayer et al., *Experientia* (1978), vol. 34.
Trown, *Cancer Research* (1980), vol. 40, p. 212.
U.S. Ser. No. 86,992 (Abandoned).
U.S. Ser. No. 219,616 (Abandoned).
EPA 253,393, Jan. 1988.
UK Application 906,000, Sep. 1962.
U.S. Ser. No. 520,166 (Pending) 1995.
Declaration of Dr. Graeme Bryce.
Declaration of Dr. Stanley Shapiro, 1996.

(List continued on next page.)

*Primary Examiner*—James H. Reamer
*Attorney, Agent, or Firm*—Sughrue, Mion, Zinn, Macpeak & Seas, PLLC

[57] ABSTRACT

Various effects of photoaging or sundamage of skin including impairment of differentiation of epidermal epithelial cells and loss of collagen fibers, abnormal changes in elastic fibers and deterioration of small blood vessels in the dermis of the skin are retarded by applying topically to the epidermis in a maintenance therapy program effective amounts of retinoids including retinoid derivatives and stereoisomers thereof such that epithelial growths are substantially reduced and prevented and the skin substantially regains and maintains its firmness, turgor and elasticity. Moreover, with persistent treatment dermal blood cells and vessels increase and the epidermis and dermis thicken, resulting in improved ability of the skin to sense, resist and recover from irritation or injury. Further, hyperpigmentation, lines and wrinkles due to aging are reduced and prevented. The treatment is particularly useful for human facial skin and preferably applied in amounts insufficient to cause excessive irritation.

11 Claims, No Drawings

OTHER PUBLICATIONS

Declaration of Nancy Bogdan, 1996.
Declaration of Corine Brown, 1996.
Order to Show Cause, PTO, Dec. 31, 1991.
Notice—Case Has Been Forwarded to the Board of Patent Appeals and Ints, PTO, Dec. 31, 1991.
Notice: Interference Assigned to EIC Downey, PTO, Dec. 31, 1991.
Identification of Lead Attorney, Bryce, Jan. 14, 1992.
Change of Lead Attorney and Associate Power of Attorney, Kligman, Jan. 24, 1992.
Associate Power of Attorney, Bryce, Jan. 27, 1992.
Unopposed Request for Extension of Time (Approved Jan. 29, 1992, Mailed Jan. 30, 1992), Bryce, Jan. 29, 1992.
Order: Party Bryce' Request for Permission to Obtain Subpoena to Take Testimony of a Witness Concerning Public Use Denied, PTO, Feb. 6, 1992.
Notice of Party–In–Interest Under 37 C.F.R. Section 1.602, Kligman, Feb. 7, 1992.
Request for One Day Extension of Time, Bryce, Mar. 2, 1992.
Bryce, et al. Response to Order to Show Cause and Request for Final Hearing, Bryce, Mar. 3, 1992.
Bryce, et al. Motion to Redefine the Interfering Subject Matter, Bryce, Mar. 3, 1992.
Communication from the Examiner–In Chief, Declaring the Captioned Interference, Dec. 31, 1991.
The Order to Show Cause, Dec. 31, 1997.
U.S.P. 4,877,805.
U.S.P. 4,603,146.
Office Action from the File History of U.S.P. 4,603,146.
Declaration of James A. Mezick, PH.D. Under 37 C.F.R. 1.132, Taken from the File History of Kligman, U.S.P. 4,877,805, Nov. 30, 1987.
U.S.P. 4,487,782.
Declaration of Albert M. Kligman, from File History of Mezick U.S.P. 4,487,782, Jul. 19, 1986.
Notice of Allowability Taken Form the File History of Kligman, U.S.P. 4,877,805.
The Declaration of Nicholas J. Lowe, from the File History of Mezick, U.S.P. 4,487,782, Jan. 1987.
Declaration of Peter M. Elias, Taken from the File history of Mezick, U.S.P. 4,487,782, Jan. 20, 1987.
Sherman, et al., "Effects of Arotinoids upon Murine Embryonal Carcinoma Cells," *Cancer Research*, vol. 43, pp. 4283–4290 Sep. 1983.
Klaus, et al., "Sulfur–Containing Arontinoids, a New Class of Retinoids," *European Journal of Medicine and Chemistry*, vol. 18, No. 5, pp. 425–429 (1983).
W. Bollag, "New Retinoids with Potential Use in Humans," *Retinoids: New Trends in Research and Therapy*, Saurat (Ed.), Retinoid Symposium, Geneva 1984, pp. 274–288, (Karger, Basel 1985).
Klaus U.S.P. 4,396,553.
Connor, et al. "A Comparative Study of the Induction of Epidermal Hyperplasia by Natural and Synthetic Retinoids," *Journal of Pharmacology and Experimental Therapeutic*, vol. 237, No. 1, pp. 31–35, 1986.
L. Kligman, "Photoaging Manifestations, Prevention, and Treatment," *Dermatologic Clinics*, vol. 4, No. 3, pp. 517–528, Jul. 1986.
The Declaration of Dr. Albert M. Kligman, Taken from the File History of Kligman, U.S.P. 4,603,146, Aug. 26, 1982.
Kligman U.S.P. 3,856,934.
Kligman, "Early Destructive Effect of Sunlight on Human Skin," *JAMA*, vol. 210, No. 13, pp. 2377–2380, Dec. 1969.
Knight Great Britain Patent Specification 1,466,062.
Information Disclosure Statement Taken from File History of Kligman, U.S.P. 4,877,805.
Great Britain Patent Specification 906,000.
Kligman, et al. "Topically Applied Tretinoin for Senile (Solar) Comedones," *Arch. Derm.*, vol. 104, pp. 420–421, Oct. 1971.
Robinson, et al., "Treatment of Solar Keratoses of the Extremities with Retinoic Acid and 5–Flourouracil," *British Journal of Dermatology*, vol. 92, pp. 703–706.
Saline, "Adventures in the Skin Trade," *Philadelphia Magazine*, vol. 71, pp. 102–133, Jul., 1980, Saline.
The 1979 Physician's Desk Reference, pp. 927–928.
Kligman, et al., "The Effect on Rhino Mouse Skin of Agents Which Influence Keratinization and Exfoliation," *The Journal of Investigative Dermatology*, vol. 73, No. 5, Part 1, pp. 354–358, 1979.
Kligman, et al., "Topical Retinoic Acid Enhances the Repair of Ultraviolet Damaged Dermal Connective Tissue," *Connective Tissue Research*, vol. 12, pp. 139–150, 1984, Kligman.
Kligman, et al., "Enhanced Repair of UV–Induced Dermal Damage by Topical Retinoic Acid", *Retinoids: New Trends in Research and Therapy*, Saurat (Ed.,) (Karger, Basel 1985).
The Great Britain Patent Specification 1,335,867.
Ashton, et al., "Histologic Changes in the Skin of the Rhino Mouse Induced by Retinoids," *Journal of Investigative Dermatology*, vol. 82, No. 6, pp. 632–635, 1984.
Copy of Stiefel U.S.P. 4,483,096.
Bryce et al Motion I. for Benefit of Earlier Filing Dates, II. to Deny Kligman Benefit of Earlier Filing Dates, Bryce, Mar. 3, 1992.
Declaration of William H. Epstein, Bryce, Mar. 3, 1992.
Notice of Service of Bryce Rule 608(B) Submission, Bryce, Mar. 3, 1992.
Declaration of Nicholas J. Lowe, M.D., Bryce, Mar. 3, 1992.
Cirriculum Vitae of Nicholas J. Lowe, M.D.
Duplicate of #12C.
Lowe, "Topical Retinoids: In Vivo Predictive Assays," *Journal of the America Academy of Dermatology*, vol. 15, No. 4, Part 2, pp. 766–772, Oct. 1986.
Duplicate of #12CC.
Duplicate of #12DD.
Duplicate of #12E.
Duplicate of #12J.
Duplicate of #12H.
Duplicate of #12K.
Bryce et al., "Selective Effect of Retinoids on The Repair of Dermal Damage and Effacement of Wrinklers in the Skin of UVB–Irradiated Hairless Mice".
Bryce et al., "The Irreversibility of Wrinkle Effacement by Retinoids in the UVB–Irradiated Hairless Mouse".
Bryce et al., "A Comparative Study of the Induction of Epidermal Hyperplasia by Natural and Synthetic Retinoids," *The Jouranal of Pharmacology and Experimental Therapeutics*, vol. 237, pp. 31–33, Apr. 1986.
Ellis et al., "Sustained Improvement with Prolonged Topical Tretinoin (Retinoic Acid) for Photoaged Skin," *Journal of the American Academy of Dermatology*, vol. 23, No. 4, Part 1, pp. 629–637, Oct. 1990.
Bhawan et al., "Effects of Tretinoin on Photodameged Skin," *Arch. Dermatol*, vol. 127, pp. 666–672, May 1991.

Declaration of Dr. Stanley Shapiro, Bryce, Mar. 3, 1992.
Curriculum Vitae of Stanley S. Shapiro, PH.D.
Duplicate of #12F.
Duplicate of #12J.
Duplicate of #16J.
Duplicate of #12M.
Duplicate of #12L.
Duplicate of #12P.
Declaration Of Dr. Graeme Bryce, Bryce, Mar. 3, 1992.
Curriculum Vitae for Graeme Bryce.
Bryce et al., "The Effect of Retinoids on the Repair Of UVB–Induced Dermal Damage in the Hairless Mouse".
Bryce et al., "Retinoic Acids Promote the Repair of the Dermal Damage and the Effacement of Wrinkles in the UVB–Irradiated Hairless Mouse," *The Journal of Investigative Dermatology*, vol. 91, pp. 175–180, 1988.
Duplicate of #6J.
Duplicate of #16K.
Duplicate of #17I.
Duplicate of #17H.
Duplicate of #16L.
Kligman et al., "Topical Tretinion for Photoaged Skin," *Journal of the American Academy of Dermatology*, vol. 15, No. 4, Part 2, pp. 836–859, Oct. 1986.
Duplicate of #16M.
Duplicate of #16N.
Letter to the Examiner with Copy of Associate Power of Attorney, Kligman, Mar. 3, 1992.
Order: Bryce Request for One Day Extentsion of Time is Granted, PTO, Mar. 4, 1992.
Motion for Extension of Time, Kligman, Mar. 30, 1992.
Motion for Extension of Time, Kligman, Apr. 29, 1992.
Motion for Extension of Time (Approved), PTO, May 4, 1992.
Opposition of Kligman to Bryce et al.'s Motion to Redefine the Interfering Subject Matter, Kligman, May 8, 1992.
Declaration of Stanley C. Bell, PH.D., Taken from the File History of U.S.P. 4,487,782, Nov. 30, 1987.
Background of Invention for U.S.P. 4,396,553.
Missing.
Amendment Taken from File History of Kligman, S.N. 610,711 Abandoned, Feb. 13, 1985.
Preliminary Amendment and Supplemental Disclosure Statement for Continuation Taken from the File History of Kligman, U.S.P. 4,877,805.
Office Action from the File History of Kligman, S.N. 205, 057, Dec. 2, 1988.
Examiner Interview Summary from File History of Kligman, S.N. 205,057, Jan. 1984.
Amendment from S.N. 205,057, Mar. 29, 1989.
Examiner Interview Summary Record from U.S.P. 4,603, 146, Oct. 17, 1985.
Amendment After Interview from U.S.P. 4,603,146, Nov. 7, 1985.
Response and Request for Declaration of Interference From S.N. 520,166, Oct. 19, 1990.
Amendment And Supplemental Response Request for Interference from S.N. 520,166, May 8, 1991.
Kligman Response to Bryce et al. Motion (I) for Benefit of Earlier Filing Dates, and (II) to Deny Kligman Benefit Of Earlier Filing Dates, Kligman, May 8, 1992.
Statement of Kligman Regarding the Bryce et al. Response to Order to Show Cause, Kligman, May 8, 1992.
Declaration of James A. Mezick, PH.D., Mezick, May 8, 1992.
Curriculum Vitae of James A. Mezick.
Kligman et al., "Topical Retinoic Acid Enhances the Repair of Ultraviolet Damaged Dermal Connective Tissue," *Connective Tissue Research*, 1984, vol. 12, pp. 139–150.
Declaration of Stanley C. Bell, Ph.D., Nov. 30, 1987.
EP 0 176 034 A2.
Dawson et al, "Synthesis and Pharmacological Activity of 6–[(E)–2–(2,6, 6–Trimethyl–1–Cyclohexen–1–YL)Ethen–1–YL]– and 6–(1,2,3,4–Tetrahydro–1,1,4, 4–Tetramethyl–6–Naphthy)–2–Naphthalenecarboxylic Acids," *Journal of Medicinal Chemistry*, 1983, vol. 26, No. 11.
Woodley et al., "Treatment of Photoaged Skin With Topical Tretinoin Increases Epidermal–Dermal Anchoring Fibrils," *JAMA*, Jun. 13, 1990, vol. 263, No. 22 Shroot: Pharmacology of Topical Retinoids, *Journal of the American Academy of Dermatology*, 1986, vol. 15, No. 4.
Background of the Invention of U.S.P. 4,396,553, Aug. 19, 1987.
U.S.P. 4,396,553.
Klaus et al., "Sulfur–Containing Arotinoids, a New Class of Retinoid," *Eur. J. Med. Chem.* 1983, pp. 425–429.
U.S.P. 4,487,782.
Mezick et al., "Topical and Systematic Effects of Retinoids on Horn–Filled Utriculus Size in the Rhino Mouse. A Model to Quantify Antikeratinizing' Effects of Retinoids," *Journal Of Investigative Dermatology*, 1984, vol. 83, No. 2.
Mezick et al., "Topical Effects of Various Retinoids on Utriculus Reduction and Cytoskelatal Protein Expression in Rhino Mouse Epidermis." R.W. Johnson Pharmaceutical Research Institute at Ortho Pharmaceutical Corporation, Raritan, NJ.
Declaration of James A. Mezick, Ph.D., Nov. 30, 1987.
Declaration of Albert M. Kligman, Jul. 19, 1986.
Declaration of Nicholas J. Lowe, Jan. 28, 1987.
Declaration of Peter M. Elias, Jan. 28, 1987.
Bollag: Experimental Data on New Retinoids. Psoriasis: Proceedings of the Fourth International Symposium, Stanford Univeristy, Jul. 6–11, 1986.
Kistler: Structure–Activity Relationship of Retinoids on the Differentiation of Cultured Chick Foot Skin, *Retinoids: New Trends in Research and Therapy*, Retinoid Symp. Geneva 1984, pp. 309–312 (Karger, Basel) 1985.
Zelickson et al., "Topical Tretinoin in Photoaging: An Ultrastructural Study," *Journal of Cutaneous Aging & Cosmetic Dermatology*, 1988, vol. 1, No. 1.
Ellis et al. "Sustained Improvement with Prolonged Topical Tretinoin (Retinoic Acid) for Photoaged Skin." *Journal of the American Academy of Dermatology*, vol. 23, No. 4, Part 1, 1990.
Declaration of Albert M. Kligman, M.D. PH.D., Kligman, May 8, 1992.
Cirriculum Vitae of Albert M. Kligman, M.D., Ph.D.
Publications of Albert M. Kligman, M.D., Ph.D.
Declaration of Nicholas J. Lowe, Jan. 28, 1987.
Declaration of Peter M. Elias, Jan. 20, 1987.
Declaration of Albert M. Kligman, Jul. 19, 1986.
Declaration of James A. Mezick, Ph.D., Nov. 30, 1987.
Declaration of Lorraine H. Kligman, PH.D., Kligman, May 8, 1992.
Cirriculum Vitae of Lorraine CT Lesnik Kligman, Jan. 10, 1992.

Kligman et al. "Topical Retinoic Acid Enhances the Repair of Ultraviolet Damaged Dermal Connective Tissue." *Connective Tissue Research*, 1984, vol. 12, pp. 139–150.
Kligman et al., "Enhanced Repair of UV–Induced Dermal Damage by Retinoic Acid." *Retinoids: New Trends in Research and Therapy*, Retinoid Symp. Geneva 1984, pp. 309–312 (Karger, Basel) 1985.
Request for Extension of Time (Papers Due Jun. 26, 1992), Bryce, May 22, 1992.
Bryce Reply to Kligman Opposition to Bryce Motion to Redefine, Bryce, Jun. 26, 1992.
Bryce U.S.P. 5,061,733, Oct. 29, 1991.
Bryce U.S.P. 5,075,333, Dec. 24, 1991.
Yu et al. U.S.P. 5,093,360, Mar. 3, 1992.
Palermo, "Retinoids" Symposium Poster, Oct., 1991, Oct. 21–24, 1991.
Declaration from a Kligman, M.D., Taken from File History of Kligman, U.S.P.4,603,146, Mar. 5, 1985.
Kligman U.S.P. 4,888,342.
Stover, et al. v. Tsai, et al., Interference No. 101,640 (Final Decision), Mar. 8, 1988.
Preliminary Amendment and Supplemental Disclosure Statement Taken from U.S.P. 4,877,805, Jun. 3, 1988.
Defendant's Memorandum in Opposition to UPI' Motion for Discovery and in Reply to the University's Statute of Limitations Memo., Univ. Patents, Inc., v. Kligman, et al. No. 89–3525 (E. D. PA. 1990).
Office Action from U.S.P. 4,603,146, May 31, 1985.
Request for Reconsideration form the File History of U.S.P. 4,877,805, Dec. 23, 1987.
Notice of Alowability and References Cited from U.S.P. 4,877,805, Mar. 1988.
Reply Declaration of Dr. Stanley Shapiro, Bryce, Jun. 26, 1992.
Duplicate of #31D.
Nair et al., "BMY 30047: A Novel Topically Active Retinoid with Low Local and Systemic Toxicity," *The Journal of Pharmacology and Experimental Therapeutics*, vol. 256, No. 1, pp. 365–370, 1990.
Reply Declaration of Dr. Graeme Bryce, Bryce, Jun. 26, 1992.
Bryce Reply to Kligman "Statement" Regarding Bryce Response to Order to Show Cause, Bryce, Jun. 26, 1992.
Motions of Kligman for Leave to File Surreply and to Strike Portions of Bryce Reply to Kligman Opposition to Bryce Motion to Redefine, Kligman, Jul. 17, 1992.
Surreply of Kligman to Bryce Reply to Kligman Opposition to Bryce Motion to Redefine, Kligman, Jul. 17, 1992.
Shapiro et al., "Evaluation of Potential Therapeutic Entities for the Treatment of Acne," *Pharmacology of Retinoids in the Skin*, vol. 3, pp. 104–112, 1989.
Shapiro et al., "Effect of Retinoids on Sabaceous Glands," *Methods in Enzymology*, vol. 190, pp. 326–333.
Doran, et al., "Retinoid Effects on Subocyte Proliferation," *Methods in Enzymology*, vol. 190, pp. 334–338.
Bryce Opposition to Kligman Motion to Strike, Bryce, Jul. 31, 1992.
Bryce Opposition to Kligman Motion for to Leave to Fie Surreply, Bryce, Jul. 31, 1992.
Kligman Replies to Bryce Oppositions to Kligman Motion to File Surreply and Motion to Strike, Kligman, Aug. 11, 1992.
Communication, Bryce, Mar. 2, 1993.
Kligman Response to Bryce et al. Communication, Kligman, Mar. 12, 1993.
Bryce Citation of in Re Van Geuns, Bryce, Apr. 5, 1993.
Kligman Response to "Bryce Citation of in Re Van Geuns", Kligman, Apr. 26, 1993.
Bryce Reply Anent in Re Van Geuns, Bryce, May 5, 1993.
Kligman Response to "Bryce Reply Anent in Re Van Geuns", Kligman, May 12, 1993.
Bryce Motion for Consideration of Newly Discovered Evidence in Connection with its Motion to Redifine, Bryce, Sep. 29, 1993.
First Amended & Supplemental Complaint Party: Ortho, Apr. 30, 1992.
Ortho's Sur–Reply Memorandum to Korff's Post–Trial Reply Memorandum Party: Ortho, Apr. 8, 1993.
Opinion and Order Party: Ortho, Sep. 23, 1993.
Motion For Unopposed Extension of Time, Kligman, Oct. 14, 1993.
Opposition of Kligman to Bryce et al.'s Motion for Consideration of Newly Discovered Evidence in Connection with its Motion to Redefine, Kligman, Nov. 2, 1993.
Declaration of Madonna M. Malin, Esq., Kligman, Nov. 2, 1993.
Deposition Excerpts—Lavker Direct.
Second Declaration of Albert M. Kligman, M.D., PH.D., Kligman, Nov. 2, 1993.
Second Declaration of James A. Mezick, PH.D, Kligman, Nov. 2, 1993.
Deposition Excerpts—Lavker Direct, 1995.
Motion for Unopposed Extension of Time, Bryce, Nov. 12, 1993.
Motion for Unopposed Extension of Time (Granted), Bryce, Nov. 15, 1993.
Bryce Reply to Kligman Opposition to Bryce Motion for Consideration of Newly Discovered Evidence, Bryce, Dec. 1, 1993.
Excerpts of Stenographers' Minutes Before Hon. Charles H. Tenney Dec. 16–17, 1992 *Ortho V. Cosprophar*.
EP 0 379 367 A2, 1987.
License Agreement Between Dr. Albert M. Kligman and Johnson & Johnson, Jul. 18, 1984.
Petition Under 37 C.F.R. §1.28(C)(2) to Accept Late Payment of Large Entity Fees, Sep. 29, 1986.
Preliminary Amendment and Supplemental Disclosure Statement from Continuation of S.N. 886,595.
Second Supplement Disclosure Statement from S.N. 205, 057, Apr. 28, 1989.
798 F.Supp. 219 (D.N.J. 1992).
Bryce Motion to Refuse Consideration of Portions of Kligman Opposition or to Compel Disclosure by Kligman, Bryce, Dec. 1, 1993.
Letter to: F. Osha, from: S. Haracz, Re: Int. No. 102,638, Nov. 10, 1993.
Letter to: S. Haracz, from: F. Osha, Re: Int. No. 102,638, Nov. 17, 1993.
Excerpts of Stenographers' Minutes Before Hon. Charles H. Tenney Dec. 16–17, 1992 *Ortho V. Cosprophar*.
EP 0 379 367 A2.
To 37 C.F.R. § 1.635 for an Extension of Time to File Kligman's Opposition, Kligman, Dec. 17, 1993.
Second Bryce Motion for Consideration of Newly Discovered Evidence in Connection with its Motion to Redefine, Bryce, Dec. 17, 1993.
European Office Action Appl No. 90 300 521.3, Jul. 27, 1992.
GB 1,466,062.

Letter to EPO from A.J. Fisher Re: European Patent Appl. No. 90300521.3, Dec. 4, 1992.
Summary of the Invention.
Information Disclosure Statement Re: USSN 886,595 Dec. 17, 1993.
Motion By the Party Kligman Pursuant To 37 C.F.R. §1.635 For An Extension Of Time To File Kligmans's Opposition (Granted), PTO, Dec. 20, 1993.
Bryce Motion to Supplement Second Bryce Motion for Consideration of newly Discovered Evidence, Bryce, Dec. 23, 1993.
European Office Action Patent No. 90300521.3–2114, Jan. 19, 1993.
International Application WO/86/06275 for "Composition and Method for Reducing Wrinkles", Nov. 6, 1986.
Correspondence from British Patent Agents to European Patent Office, May 19, 1993.
Wilmott U.S.P. 4,826,828, May 2, 1989.
Background of Invention from File History of U.S.P. 4,826, 828, Feb. 15, 1985.
Background of Invention from File History of U.S.P. 4,826, 828 (CIP), Apr. 22, 1985.
Background of Invention form File History of U.S.P. 4,826, 828 (CIP), Mar. 1986.
Kligman Opposition to Bryce Motion to Refuse Consideration of Portions of Kligman Opposition or to Compel Disclosure by Kligman, Kligman, Dec. 28, 1993.
Motion for Extension of Time, Kligman, Jan. 5, 1994.
Motion for Extension of Time (Granted), PTO, Jan. 10, 1994.
Motion for Unopposed Extension of Time, Bryce, Jan. 12, 1994.
Motion for Unopposed Extension of Time (Granted), PTO, Jan. 12, 1994.
Motion for Extension of Time, Kligman, Jan. 13, 1994.
Motion for Extension of Time (Granted), PTO, Jan. 14, 1994.
Bryce Reply to Kligman Opposition to Bryce Motion to Refuse Consideration of Portions of Kligman Opposition or to Compel Disclosure by Kligman, Bryce, Jan. 18, 1994.
Ortho Pharmaceutical Corp. and Johnson & Johnson v. St. Ives Laboratories—Compliant for Trademark Infringement, Sep. 1988.
Ortho & J&J v. St. Ives Motion, Nov. 25, 1988.
Declaration of Howard Maibach, M.D. For "Ortho" Case, Oct. 24, 1988.
Declaration of Madonna M. Malin for "Ortho" Case, Nov. 14, 1988.
Motion for Extension of Time, Kligman, Jan. 24, 1994.
Motion for Extension of Time (Granted), PTO, Jan. 24, 1994.
Motion for Extension of Time, Kligman, Feb. 17, 1994.
Motion for Extension of Time (Granted), PTO, Feb. 22, 1994.
Kligman Opposition to Second Bryce Motion for Consideration of Newly Discovered Evidence and Bryce Motion to Supplement Second Bryce Motion for Consideration of Newly Discovered Evidence, Kligman, Mar. 18, 1994.
European Patents Handbook Chartered Institute of Patent Agents, Second Ed. vol. 1, 1993.
Second Declaration of Albert Kligman, M.D., Ph.D., Mar. 18, 1994.
Second Declaration of Lorraine Kligman, Ph.D., With Exhibits, Mar. 17, 1994.
Declaration of William W. Schwartze, with Exhibits, Mar. 17, 1994.
Unopposed Motion for Extension of Time, Bryce, Mar. 30, 1994.
Bryce Motion for Leave to File Unredacted Kligman Exhibits and for Expedited in Camera Hearing, Bryce, Apr. 8, 1994.
Letter to Counsel for Kligman from Haracz, Mar. 24, 1994.
Letter to Hatacz from Counsel for Kligman, Mar. 30, 1994.
Unredacted Copy of Johnson & Johnson Memo, Mar. 18, 1994.
Letter to Dr. Kligman from Johnson & Johnson's Director of Medical Affairs, Mar. 15, 1984.
Kligman Opposition in Part to Bryce Motion for Leave to File Unredacted Kligman Exhibits and for Expedited in Camera Hearing, Kligman, Apr. 18, 1994.
Bryce Reply to Kligman Opposition to Second Bryce Motion for Consideration of Newly Discovered Evidence and Bryce Motion to Supplement Second Bryce Motion for Consideration of Newly Discovered Evidence, Bryce, May 2, 1994.
Stenographer's Minutes, Mar. 17, 1993.
Conner: Study Report—Retinoic Acid Formatting in Human Epidermis from Retinal and Retinyl Palmitate Offer Multiple Applications in a Cream Vehicle.
Preliminary Amendment and Supplemental Disclosure Statement (205,057), Sep. 20, 1988.
Letter to J.Frank Osha, Apr. 25, 1994.
Johnson & Johnson Memo to Bodine, Re: Retinoic Acid in Aged Skin, Feb. 28, 1974.
Letter to Dr. Kligman, May 15, 1974.
Letter to Dr. Kligman, Mar. 26, 1986.
Notes from Meeting with Dr. Kligman, Apr. 10, 1986.
Letter to Dr. Kligman, Jun. 23, 1986.
Letter to Dr. Kligman, Jul. 11, 1986.
Letter to J.Frank Osha, Apr. 4, 1994.
Letter to Stephen Haracz, Apr. 5, 1994.
Letter to Dr. Kligman, Jul. 18, 1986.
Appeal of Office Action from European Patent Office, Aug. 9, 1993.
European Patent Application 0 379 367.
Kligman, "The Hairless Mouse and Photoaging," *Pharm. and Pharm.* 54:1109–1118.
Office Action (886,595), Jun. 2, 1987.
Decl 37 CFR 1.132 of Dr. James A. Mezick, Nov. 30, 1987.
Letter to J. Frank Osha, Apr. 5, 1994.
Letter to Stephen Haracz, Apr. 22, 1994.
USP 4,877,805.
Bryce Reply to Kligman Opposition in Part to Bryce Motion for Leave to File Unredaccted Kligman Exhibits, Bryce, May 3, 1994.
Order, PTO, Sep. 26, 1995.
Bryce et al. Motion for Extension of Time 37 CFR 1.645, Bryce, Nov. 2, 1995.
Kligman Motion for Extension Of Time 37 CFR 1.645, Kligman, Dec. 4, 1995.
Kligman Motion for Extension of Time 37 CFR 1.645 Granted, PTO, Dec. 8, 1995.
Bryce et al. Motion for Extension of Time 37 CFR 1.645 and 1.635, Bryce, Jan. 11, 1996.
Bryce et al. Motion for Extension of Time 37 CFR 1.645 and 1.635 Granted, PTO, Jan. 22, 1996.
Bryce et al. Motion for Extension of Time 37 CFR 1.645 and 1.635, Bryce, Feb. 2, 1996.
Order, PTO, Feb. 16, 1996.

Contingent Abandonment of Contest, Kligman, Feb. 28, 1996.
Bryce Opposition to Kligman "Contingent" Abandonment of Contest, Bryce, Mar. 4, 1996.
Bryce Preliminary Motion I, Bryce, Mar. 6, 1996.
Bryce Preliminary Motion II, Bryce, Mar. 6, 1996.
Bryce Preliminary Motion III, Bryce, Mar. 6, 1996.
Bryce Preliminary Motion IV, Bryce, Mar. 6, 1996.
Bryce Preliminary Motion V, Bryce, Mar. 6, 1996.
Bryce Preliminary Motion VI, Bryce, Mar. 6, 1996.
Bryce Preliminary Motion VII, Bryce, Mar. 6, 1996.
Second Declaration of Nicholas J. Lowe, Bryce, Mar. 6, 1996.
Dr. Nicholas J. Lowe—Biographical Resume.
Duplicate of #12Z, Jul. 1980.
Preliminary Amendment and Supplemental Disclosure Statement S.N. 205,057, Sep. 20, 1988.
Armstrong et al., "Clinical Panel Assessment of Photodamaged Skin Treated with Isotretinoin using Photographs," *Arch. Dermatol.* 128:352–356 (1992).
Bryce et al. JID 90,549 (1988).
Bryce et al. JID 96,585 (1991).
Duplicate Of #31D.
Griffiths, "To Concentrations of Topical Tretinoin (Retinoic Acid) Cause Similar Improvement of Photoaging But Different Degrees of Irritation," *Arch. Dermatal.* 131:1037–1044 (1995), Sep. 1995.
Duplicate of #18L.
Declaration of Graeme F. Bryce, Bryce, Mar. 6, 1996.
Lab Notebook #13976P.87–98, Effect of Ro4–3780 and UV–B . . . Mice.
Lab Notebook #15521P.15–26, Effect of Ro4–3780 and Ro15–0778 UV–B . . . Mice.
Clinical Research 35, 672A(1987), 1987.
Duplicate of #18F.
Declaration of Nancy Bogdan, Bryce, Mar. 6, 1996.
Exhibits Accompanying Bryce Preliminary Motions I–VII, Bryce, Mar. 6, 1996.
Specifications/Abstract S.N. 297,388, Aug. 28, 1981.
Specifications/Abstract S.N. 610,711.
Preliminary Amendment S.N. 753,505.
Specifications/Abstract S.N.205,157, Jul. 16, 1986.
Request for FWC, Jun. 3, 1988.
USP 4,603,146.
38 PDR 1437–8, 1984.
Letter to J. Frank Osha Re: Unredacted Documents, Apr. 4, 1994.
Letter to Stephen M. Haracz, Apr. 5, 1994.
Letter to Dr. Kligman, Mar. 26, 1986.
Notes from Meeting with Dr. Kligman, Apr. 10, 1986.
Letter to Dr. Kligman, Jun. 23, 1986.
Letter to Dr. Kligman, Jul. 11, 1986.
Declaration, Power of Attorney, Jul. 16, 1986.
Letter to Dr. Kligman, Jul. 18, 1986.
European Patent Application 0 176 034.
European Patent Application 0 176 035.
European Patent Application 0 176 032.
Duplicate of #24A.
USP 4,806,558.
Duplicate of #31A.
USP 4,760,174.
Duplicate of #29B, 1984.
Duplicate of #12N.
Notes Form Experiment 104 Hr.
Letter to Dr. James Mezick, Nov. 3, 1986.
Illustrated Stedman's Medical Dictionary 24ed P.929.
Office Action S.N. 886,595, Jun. 2, 1987.
Declaration Under 37 CFR 1.132 of Dr. Jamie A Mezick, Nov. 30, 1987.
Notice of Allowance and Issue Fee Due S.N. 886,575, Mar. 4, 1988.
Duplicate of #12G.
Declaration of Albert Kligman, Jul. 19, 1986.
Declaration of Nicholas J. Lowe, Jan. 28, 1987.
Declaration of Peter M. Elias, Jan. 28, 1987.
First Amended and Supplemental Complaint Ortho et al. v. Cosprophar, Apr. 30, 1992.
Second Declaration of Albert M. Kligman, Oct. 29, 1993.
Second Declaration of James A Mezick PH. D., Nov. 1, 1993.
Dr. Nicholas J. Lowe Biographical Resume.
Bryce et al., "Selective Effect of Retinoids on the Repair of Dermal Damage and Effacement of Wrinkles in the Skin of UVB–Irradiated Hairless Mice." JID 90,549 (1988).
Bryce et al., "The Irreversibility of Wrinkle Effacement by Retinoids in the UVB–Irradiated Hairless Mouse," JID 96,585 (1991).
32 F3d 690.
First Amended and Supplemental Complaint, Apr. 30, 1992.
Duplicate of #12P.
Duplicate of #31D.
Duplicate of #95J.
Duplicate of #18L.
33 PDR 927–8 (1979).
Duplicate of #12Z.
Preliminary Amendment and Supplemental Disclosure Statement S.N. 205,057, Sep. 20, 1988.
Office Action S.N. 205,057, Nov. 29, 1988.
Amended Complaint and Demand for Jury Trial University Patents v. Kligman et al., Oct. 3, 1989.
20 USPQ2d 1401.
Defendants' Amended Answer and Counterclaim, Dec. 13, 1983.
Defendants' Memorandum in Opposition to UPI Motion for Discovery and in Reply to the University Statute of Limitation Memo, Mar. 23, 1990.
Letter to Dr. Gerald S. Lazarus, Oct. 16, 1985.
Reply Affidavit of Albert M. Kligman, Mar. 23, 1990.
Docket as of 02/1192, Feb. 11, 1992.
Letter to J Frank Osha, Nov. 10, 1993.
Letter to Stephen M Haracz, Nov. 17, 1993.
Complaint for Trademark Infringement, Sep. 7, 1988.
European Patent Application 0 379 367.
USP 3,932,665.
Amendment S.N. 610,711, Feb. 13, 1985.
Kligman, *JAMA* 210:2377–2380 (1969).
Duplicate of #12Q.
UK 1 466 062.
Duplicate of #12G.
USP 4,843,096.
New Application S.N. 944,119.
Declaration, Power of Attorney, Dec. 16, 1986.
European Patent Application 0 274 104.
Amendment and Statement of Prior Art S.N. 944,119, Apr. 21, 1988.
Office Action S.N. 944,119, Oct. 17, 1988.
UK 1 335 867, Oct. 17, 1988.
Notice of Abandonment for S.N. 944,119, May 17, 1989.
Clinical Research 35, 672A(1987).
Duplicate of #96F.

Armstrong et al., *Arch Dermatol* 128:352–356 (1992).
Sendagorta et al., "Topical Isotretinoin for Photodamaged Skin," *J.AM. Acad. Dermatol.* 1992;27:S15–S18, 1992.
Examiner Interview Summary Record, Jan. 27, 1989.
Amendment S.N. 205,057, Apr. 3, 1989.
USP 4,826,828.
Bryce Notice of Intent to Rely upon Previously Filed Documents, Bryce, Mar. 6, 1996.
Notice of Filing the Bryce Preliminary Statement, Bryce, Mar. 6, 1996.
Notice of Filing Preliminary Statement, Kligman, Mar. 6, 1996.
Preliminary Statement of Senior Party Kligman Under 37 CFR § 1.622 and 1.623, Kligman, Mar. 6, 1996.
Order, PTO, Mar. 25, 1996.
Kligman's Motion Under 37CFR § 1.635, Kligman, Mar. 26, 1996.
Kligman Notice of Filing Reissue Application—37 CFR § 1.662(b)Submitted with Copies of Request for Title Report, Offer to Surrender Letters Patent under 37 CFR § 1.178, Reissue Filing Letter and Reissue Specification, Kligman, Apr. 2, 1996.
Byrce's (I) Opposition to Kligman Rule 635 Motion and (II)Response to Kligman Request for Entry of Adverse Judgment, Byrce, Apr. 4, 1996.
Kligman Reply in Support of its Motion under 37 C.F.R. § 1.635, Kligman, Apr. 15, 1996.
Notice of Settlement of Interference and Withdrawal of Bryce Opposition Paper Filed Apr. 4, 1996, Jun. 6, 1996.
Judgment, PTO, Sep. 30, 1996.
Redeclaration, PTO, Sep. 30, 1996.
Joint Filing of Interference Settlement Agreement and Request to Keep Separate from Interference File, Nov. 26, 1996.
Communication, PTO, Dec. 6, 1996.
Communication, PTO, Jan. 6, 1997.

METHODS FOR TREATMENT OF SUNDAMAGED HUMAN SKIN WITH RETINOIDS

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation of application Ser. No. 886,595, filed July 16, 1986, now abandoned, which in turn is a continuation-in-part of my U.S. Pat. Application Ser. No. 759,505, filed July 26, 1985, entitled, "Methods for Retarding the Effects of Aging of the Skin," now U.S. Pat. No. 4,603,146, which was a continuation of application Ser. No. 610,711, filed May 16, 1984, now abandoned, which, in turn, was a continuation-in-part of application Ser. No. 297,388, filed Aug. 28, 1981, entitled "Composition and Method for Improving the Quality of Human Skin and Skin Aging Retardant", now abandoned.

FIELD OF THE INVENTION

This invention relates to methods using retinoids to retard the effects of aging of the skin and generally improve the quality of the skin, particularly human facial skin.

BACKGROUND OF THE INVENTION

Caucasians who have had a good deal of sun exposure in childhood will show the following gross cutaneous alterations in adult life: wrinkling, leatheriness, yellowing, looseness, roughness, dryness, mottling (hyperpigmentation) and various premalignant growths (often subclinical). These changes are most prominent in light-skinned persons who burn easily and tan poorly. The baleful effects of sunlight are cumulative, increasing with time often referred to as "photoaging". Although the anatomic degradation of the skin is most advanced in the elderly, the destructive effects of excessive sun exposure are already evident by the second decade. Serious microscopic alterations of the epidermis and dermis occur decades before these become clinically visible. Wrinkling, yellowing, leatheriness, loss of elasticity are very late changes.

Retinoids (e.g. Vitamin A and its derivatives) are substances which are known to have a broad spectrum of biological activity. Most specifically, these substances affect cell growth, differentiation and proliferation. Retinoids affect the differentiation, maintenance, and proliferation of many types of cells whether they are of ectodermal, endodermal or mesodermal origin; whether they are epithelial, fibroblastic or mesenchymal; or whether they are neoplastic, preneoplastic or non-neoplastic. At present, retinoids have found clinical utility in the treatment of severe cystic acne, psoriasis, and other disorders of keratinization. Possible uses of retinoids are being explored in the prophylaxis and treatment of cancer. For a review of developments in retinoid therapy, see Pawson, B. A. et al. "Retinoids at the Threshold: Their Biological Significance and Therapeutic Potential", Journal of Medicinal Chemistry 25:1269–1277 (1982).

The present status of retinoids in research and clinical medicine can be found in the publication of a symposium held in Geneva: J. H. Saurat. Editor, "Retinoids: New Trends in Research and Therapy," Karger Publishing Co. (1985).

It is known to use certain retinoids, particularly vitamin A acid, topically for treatment of acne as set forth in my U.S. Pat. No. 3,729,568. Other known topical uses of vitamin A acid were reviewed by Thomas, J. R., et al. "The Therapeutic uses of Topical Vitamin A Acid", Journal of American Academy of Dermatology 4:505–516 (1981) include, in addition to acne treatment, treatment of senile comedones, nevus comedonicus, linear verrucous nevus, plantar warts, pseudofollicultis, keratoacanthoma, solar keratosis of extremities, callosites, keratosis palmaris et plantaris. Darier's disease, ichthyosis, psoriasis, acanthosis nigricans, lichen planus, molluscum contagiosum, reactive perforating collagenosis, melasma, corneal epithelial abrasion, geographic tongue, Fox-Fordyce disease, cutaneous metastatic melanoma and keloids or hypertrophic scars.

It is believed that retinoids influence ultrastructural and proliferative properties of epidermal cells. However, these prior art uses of vitamin A acid have generally involved short term treatments in which relatively high concentrations retinoic acid are applied (i.e. sufficient to cause significant irritation and often peeling) in order to obtain a quick therapeutic effect of the particular condition, such as removal of comedones, as opposed to long-term treatment of normal aging or photographing skin.

My copending application Ser. No. 759,505 discloses methods for treating sundamaged human skin topically with vitamin A acid in an emollient vehicle in such amounts as to be essentially non-irritating to the skin. This treatment causes the skin, particularly human facial skin, to substantially regain and maintain its firmness, turgor and elasticity by retarding and reversing the skin's loss of collagen fibers, abnormal changes in elastic fibers, deterioration of small blood vessels, epidermal atrophy and formation of abnormal epithelial growths.

BRIEF SUMMARY OF THE INVENTION

The present invention relates to the use of other retinoids, as hereinafter defined, in moderating and preventing the aging changes of the exposed (sundamaged) areas of the skin, especially the face. In particular, the methods of the present invention retard the effects of photoaging of the skin due to thinning and abnormal differentiation of the epidermis, inter alia. In general, the present invention relates to methods for retarding and reversing the loss of collagen fibers, abnormal changes in elastic fibers, deterioration of small blood vessels, and formation of abnormal epithelial growths in sundamaged human skin, comprising applying topically to the surface of the skin a composition comprising effective amounts of a retinoid in an emollient vehicle in a program of maintenance therapy, whereby the skin substantially regains and maintains its firmness, turgor and elasticity during the therapy, the composition and amounts of retinoid therein being selected so as to provide a sub-irritating dose for application.

More specifically, the methods comprise the topical application to the surface of the skin of effective amounts of retinoids in a program of maintenance therapy, whereby epithelial neoplasms (basal and squamous cell cancers) and pre-neoplastic growths (actinic keratoses) are substantially prevented. Also, the skin significantly regains and maintains its firmness, turgor and elasticity during the therapy. Effacement of fine wrinkles is an important clinical effect. Generally, the maintenance therapy is begun in adult life when epithelial growths and other aging changes begin to appear clinically. Pigmentary blotching and mottling are also alleviated.

The retinoids may be applied to the skin in any non-toxic, dermatologically acceptable vehicle, preferably a nonvolatile, emollient or lubricating vehicle, in an amount and at a frequency which are insufficient to cause irritation of the skin. Generally, the concentrations are low but may be suitably varied depending on the relative strength of the applied retinoid.

DETAILED DESCRIPTION OF THE PREFERRED EMBODIMENTS

The purpose of this invention is to moderate and retard the aging changes in the skin by topical application of retinoids beginning in young adult life when aging characters (sundamage) first become evident clinically. Certain anatomic alterations can be corrected and at least partially reversed, accompanied by improvement in the appearance of the skin.

The invention accomplishes two goals. First, a prophylactic effect in preventing progression and worsening of the damage with the passage of time. Secondly, various abnormalities are corrected and modified to the extent that the structure and function of the skin acquires the characteristics of younger (undamaged) skin.

AGE ASSOCIATED STRUCTURAL CHANGES

Although many of the effects of the aging of the human skin are the result of underlying structural changes which build up over a period of years and can only be detected histologically prior to young adult life, these changes and effects begin to appear clinically in young adults, namely those between about 20 and 30 years of age, and are generally evident about middle age, namely between about 35 and 45 years of age, and become more and more evident and pronounced thereafter, especially in persons excessively exposed to sunlight. The more apparent effects of aging have already been referred to above; and each is associated with one or more underlying structural changes in the skin. For example, blotchiness or mottling (hyperpigmentation) is due to accumulation of melanin in the basal cells of the epidermis. This happens because the reproduction of the cells slows down greatly with aging, allowing them much longer time to receive melanin from the surrounding pigment-producing melanocytes. By stimulating the proliferation of basal cells, pigment retention is prevented.

In addition to obvious cosmetic improvements in the skin, there are a number of other changes which are more important though less apparent, including loss of sensory acuity, reduced wound healing, decreased blood flow and decrease in the thickness of the skin. Older people have less sensitivity to pain and a longer response time. Thus, pain due to irritation or injury is not felt as soon or to the same extent as in young people with the result that superficially minor but potentially serious injuries may be sustained without the individual being aware of the injury until serious damage has occurred.

The surface temperature of the skin in older people is lower than the skin temperature in younger people, so that they often feel cold. This is one reason why the elderly retire to the sun-belt. Anatomically there is a great loss of small blood vessels so that physiologically the blood flow through the skin is greatly reduced. The skin becomes paler and cooler. Furthermore, the decreased blood supply decreases the rate at which irritants and toxins are cleared from the skin. Dangerous build-up of toxic agents can result.

Still further, the skin of older people is more easily torn than that of younger people, since both the epidermis and dermis become thinner with age and the fibrous matrix becomes structurally inferior. As a result, there is less bulk to protect underlying organs and therefore more risk of serious injury. Moreover, when wounds or injuries are sustained, healing of the wounds is much slower in older people.

The underlying causes of the above gross skin effects may be understood more readily from the following discussion of the specific changes in the epidermis and dermis as aging progress 1. Epidermis With increasing age and exposure of a human to sun and other environmental traumas, cells divide at a slower rate (decreased capacity to renew themselves). They show marked irregularities in size, shape and staining properties; orderliness (polarity) from below to above is lost. The thickness of the epidermis decreases (atrophy). The horny layer which comprises the barrier against water loss and penetration of chemicals becomes abnormal due to the shedding (exfoliation) of cells in large groups or clusters instead of as individual cells, resulting in roughness, scaling and dryness. There is loss of the orderly transformation of living epithelial cells into cornified dead cells which are shed at the surface, that is, differentiation is impaired. Aberrant differentiation results in numerous foci of abnormal epithelial growths or tumors, the most frequent of which are actinic keratoses. After many years these can transform into frank skin cancers called basal cell and squamous cell cancers. Pigment producing cells (melanocytes) can also become altered, forming flat, dark growths (lentigo melanoma) which may progress to malignant melanoma. The cells which make up these permalignant growths are eliminated by topical application of retinoids.

2. Dermis

The cells which make up the fibers of the dermis become smaller and sparser with increasing age, usually in sundamaged facial skin. There is a great loss of collagen fibers resulting in looseness and easy stretchability of the skin; elastic fibers become abnormal so that the skin does not promptly snap back after being stretched. Since the fibrous components comprise more than 90% of the bulk of skin of which 95% is collagen, the degradation of these fibers, especially collagen, is mainly responsible for wrinkling, laxness and loss of elasticity.

Small blood vessels become thin walled, dilated and often ruptured. Vascular supply thereby becomes compromised.

Beneficial Effects of Retinoids in Accordance With the Present Invention (a) Increased proliferative activity of epidermal cells. This results in thickening of the epidermis with correction of atrophy. Cell renewal is quickened so that cells divide at a rate typical of younger skin. Treatment with retinoids in accordance with the invention can double the thickness of the epidermis. The stimulation of cell growth also results in faster wound healing. Experiments have been performed wherein blisters have been raised and the roofs cut off of the skins of individuals of various ages. Healing takes place in 2 or 3 weeks in young people, but takes much longer in older persons. Application of the retinoid tretinoin, vitamin A acid or all-trans retinoic acid before raising the blister halves the healing time.

(b) Correction of abnormalities of differentiation. Retinoids regulate and control the physiologic behavior of epithelial tissue, assuring its stability and integrity. They correct and normalize abnormalities of differentiation. In sundamaged skin, the numerous foci of abnormal growth and segments of atypical, abnormal epidermis are corrected, reversed or eliminated. Fewer growths appear and progression to cancer is halted. Normalizing of the epidermis results in a smoother, less dry and rough skin, since cells are not only produced more rapidly, but exfoliation occurs by individual cells rather than in clusters or scales, thus improving the topography of the skin. Moreover, hyperpigmentary blotches and splotches are reduced by retinoids, eliminating the mottled appearance of sundamaged skin.

(c) The metabolism of fibroblasts is increased. Fibroblasts synthesize the fibers of the dermis; new collagen is laid down, strengthening the physical foundation of the skin. Fibroblasts also make the ground substance which exists between the fibers, allowing these to glide past each other. The ground substance, known as acid mucopolysaccharides, is also responsible for the turgor and bounce of the skin. Retinoids stimulate the formation of new acid mucopolysaccharides.

Accordingly, retinoids promote the formation of a more normal dermis. Because of this activity, they have been found to promote and accelerate the healing of wounds in compromised tissue, of which aged dermis is an example. Further, the production of a new collagen layer not only repairs damaged skin but results in the effacement and prevention of fine wrinkles and lines.

(d) Vascularity is increased. Retinoids stimulate blood flow and promote the formation of new vessels. Blood flow is greatly reduced in aged, sundamaged skin. A brisker blood supply improves the physiologic competence of the skin and imparts a livelier, glowing appearance. Patients often say their skin feels "more alive".

Several of the prior art treatments using retinoic acid as referred to above have claimed there is an increase in the blood flow in the skin. However, the increased blood flow from such short term treatments could result simply from vasodilation caused by the irritating effects of high concentrations of the acid. In contrast, the low sub-irritating concentrations of retinoids according to the present invention do not cause significant vasodilation. Over the long term there occurs formation of many new small blood vessels, markedly increasing the functional blood supply to the skin. As a result, the skin can react more effectively to external sources of damage and can then mount a more normal inflammatory response to fight infection. The increased blood supply allows the skin to clear irritants and toxins more quickly.

Still further, treatment with retinoids according to the present invention raises the surface temperature of the skin by about ½ degree centigrade due to greater flow of blood. The increased blood flow also increases acuity to pain and irritation, and the skin becomes more reactive to chemical insults. For example, experiments with highly drying and irritating cosmetics, soaps, perfumes, etc. have shown that young people will experience severe irritation within 3 or 4 days whereas it may take 2 to 3 weeks for an older person to note the same irritation. The increased sensitivity of the skin treated with retinoids provides an early warning system to older people so that too much damage is not done before the pain or irritation is felt.

Retinoids have been defined narrowly as comprising simply vitamin A (retinol) and its derivatives such as vitamin A aldehyde (retinal), vitamin A acid (retinoic acid), comprising the so called natural retinoids. However, subsequent research has resulted in a much larger class of chemical compounds that are termed retinoids due to their biological similarity to vitamin A and its derivatives. Compounds useful in the present invention include all natural and/or synthetic analogues of vitamin A or retinol-like compounds which possess the biological activity of vitamin A in the skin, such as the control of epithelial cell differentiation of keratinocytes in the epidermis and/or stimulation of fibroplasia or new collagen synthesis in the dermis among other effects. Accordingly, as used herein for purposes of the present invention, the term "retinoid" will be understood to include any of the foregoing compounds. Examples of suitable retinoids for use in the present invention are set forth in Table I, although it will be understood that the invention is not limited thereto.

TABLE 1

| Chemical, Common and/or Commercial Name |
|---|
| Isotretinoin |
| 13-cis-retinoic acid |
| ACCUTANE |
| Etretinate |
| TEGISON |
| (all-E)-9-(4-methoxy-2,3,6-trimethylphenyl)-3,7-dimethyl-2,4,6,8-nonatetraenoic acid ethyl ester |
| Etretin |
| (all-E)-9-(4-methoxy-2,3,6-trimethylphenyl)-3,7-dimethyl-2,4,6,8-nonatetraenoic acid |
| Motretinate |
| N-ethyl-9-(4-methoxy-2,3,6-trimethylphenyl)-3,7-dimethyl-2,4,6,8-monotetraenamide |
| (E,E)-9-(2,6-dichloro-4-methoxy-3-methylphenyl)-3,7-dimethyl-2,4,6,8-nonatetraenoic acid ethyl ester |
| 7,8-didehydroretinoic acid |
| (E,E)-4-[2-methyl-4-(2,6,6-trimethyl-1-cyclohexane-1-yl)-1,3-butadiamyl] benzoic acid |
| (E,E)-4-[4-methyl-6-(2,6,6-trimethyl-1-cyclohexane-1-yl)-1,3,5-hexatrienyl] benzoic acid |
| (all-E)-3,7-dimethyl-9-(3-thienyl)-2-4,6,8-nonatetraenoic acid |
| (E,E,E)-3-methyl-7-(5,6,7,8-tetrahydro-5,5,8,8-tetramethyl-2-naphthalenyl)-2,4,6-octatrienoic acid |
| (E)-6-(2,6,6-trimethyl-1-cyclohexen-1-yl)ethenyl)-2-naphthalenecarboxylic acid |
| (E,E,E)-7-(2,3-dihydro-1,1,3,3-tetramethyl-1H-inden-5-yl)-3-methyl-2,4,6-octatrenoic acid |
| (E)-4-[2-(2,3-dihydro-1,1,3,3-tetramethyl-1H-inden-5-yl)-1-propenyl) benzoic acid |
| TTNPB |
| (E)-4-[2-(5,6,7,8-tetrahydro-5,5,8,8-tetramethyl-2-naphthalenyl-1-propenyl] benzoic acid |
| (E)-4-[2-(5,6,7,8-tetrahydro-3-methyl-5,5,8,8-tetramethyl-2-naphthalenyl-1-propenyl] benzoic acid |
| (E)-1,2,3,4-tetrahydro-1,1,4,4,-tetramethyl-6-(1-methyl-2-phenylethenyl) naphthalene |
| 6-(1,2,3,4-tetrahydro-1,1,4,4-tetramethyl-6-naphthyl)2-naphthalenecarboxylic acid |
| (E)-6-[2-[4-(ethylsulfonyl)phenyl]-1-methylethenyl]-1,2,3,4-tetrahydro-1,1,4,4,-tetramethylnaphthalene |
| 4-[(5,6,7,8-tetrahydro-5,5,8,8-tetramethyl-2-naphthalenyl)ethynyl] benzoic acid |
| (E)-2-(1,1,4,4-tetramethyl-1,2,3,4- |

TABLE 1-continued

| Chemical, Common and/or Commercial Name |
|---|
| tetrahydronaphth-7-yl)-]-i-[4-tetrazol-5-yl)phenyl)-1-propene |
| (E)-4-[2-(5,6,7,8-tetrahydro-7-hydroxy-5,5,8,8-tetramethyl-2-naphthalenyl)-1-propenyl] benzyl alcohol |

Also encompassed within the term "retinoid" are geometric and stereoisomers of the retinoids. For example, in my co-pending application Ser. No 759,505 in which vitamin A acid was used as the active ingredient, the specific examples used tretinoin ( all-trans retinoic acid). However, according to the present invention it has been found that isotretinoin (13-cis-retinoic acid) may also be used, although somewhat higher concentrations are needed to obtain equivalent results.

Retinoids may be formulated in bland, moisturizing bases, such as creams or ointments, usually in low concentrations, although higher concentrations may be used for darker skins. For example, isotretinoin may be used in concentrations of about 0.01% to 0.3% and preferably about 0.04% to 0.1% by weight of the base.

Other non-toxic, dermatologically acceptable vehicles or carriers in which retinoids are stable will be evident to those of ordinary skill in the art. In general, emollient or lubricating vehicles, such as oleaginous substances, which help hydrate the skin are preferred. As used herein, the term "emollient" will be understood to refer to the non-irritating character of the composition as a whole. That is, the nature of the vehicle and amount of retinoid therein should be selected so as to provide a sub-irritating dose for topical application. Volatile vehicles which dry or otherwise harm the skin, such as alcohol and acetone, should be avoided.

An ointment base (without water) is preferred in the winter and in subjects with very dry skin. Examples of suitable ointment bases are petrolatum, petrolatum plus volatile silicones, lanolin, and water in oil emulsions, such as Eucerin (Beiersdorf).

In warm weather and often for younger persons, oil in water emulsion (cream) bases, are preferred. Examples of suitable cream bases are Nivea Cream (Beiersdorf), cold cream (USP), Purpose Cream (Johnson & Johnson), hydrophilic ointment (USP), and Lubriderm (Warner-Lambert).

Some retinoids are mild irritants and may cause redness and scaling, which may be accompanied by some tenderness and tightness. These reactions are transient and quickly disappear when the applications are stopped. However, the skin rapidly accommodates, and even when retinoids are applied excessively to produce visible inflammation, the reaction slowly disappears leaving no permanent sequellae. Systemic side reactions are unknown and are not to be expected from such low concentrations according to the present invention. Selection of an appropriate emollient vehicle will more readily allow the use of a highly effective but sub-irritating dose of the retinoid.

The length of treatment according to the present invention may best be described as indefinite. That is, compared to the short term prior art treatments of various conditions with retinoids in which the treatments were terminated as soon as the condition cleared, the present invention requires treatment to be continued indefinitely since the aging process continues indefinitely. Also, the benefits of treatment slowly fade after the treatment is stopped. The treatment of the present invention may be considered to be intervention therapy in decelerating the aging process. If the intervention is stopped, there is regression to the original state. Hence, a maintenance regimen is required.

Usually, there is little point in beginning the treatments of the present invention until young adult life or, more typically, in middle age, when the effects of aging begin to appear. The particular program of maintenance therapy according to the present invention will vary depending upon the individual and conditions being treated. Generally, depending upon the age and state of the skin when treatments begin, it has been found that once a day applications of retinoids for up to 6 to 8 months may be necessary to reduce and control the effects of aging which have already occurred. Once a stabilized skin control has been obtained, the frequency of application of the retinoids may be reduced, for example to two or three times a week, and in some cases only once a week for the rest of the person's life. That is, once the aging process has been controlled, a maintenance dose on the order of two applications per week is generally sufficient to maintain that state.

The invention will now be illustrated in more detail by reference to the following specific, non-limiting examples:

EXPERIMENTAL EXAMPLE 1

Twenty-six middle-aged women, 35 to 55 years old, with actinically damaged skin, received once daily applications to the entire face of 0.05% 13-cis-retinoic acid in Purpose Cream for a period of 4 to 6 months. All had wrinkles, blotches and elastosis. The treatment caused neither redness nor drying of the skin. The treatment also was better tolerated than similar treatments with 0.05% all-trans retinoic acid in a cream base as disclosed in my co-pending application. The application f 13-cis-retinoic acid resulted in smoother skin in which fine wrinkles were moderately effaced.

EXPERIMENTAL EXAMPLE 2

Applications were made in the same way as Example 1 with 0.25% 13-cis-retinoic acid in Purpose Cream to the faces of eight women with photodamaged skin. The treatment was better tolerated (less irritancy was noted) than similar treatments of 0.05% tretinoin in a cream base as disclosed in my co-pending application. The treatment resulted in the obvious elimination of fine wrinkles. In addition, the skin appeared to have greater turgor to the palpating finger. The subjects of the study expressed satisfaction with the results of the treatment. The experimental results indicate that the application of 0.25% 13-cis-retinoic acid in Purpose Cream to be about as effective as 0.05% tretinoin in a cream base. Thus, 13-cis-retinoic acid has the capacity to achieve the same beneficial effects as retinoic acid on photoaged skin. Since the 13-cis-retinoic acid is apparently less effective at equal concentrations, biological equivalence can be obtained by increasing the concentration of 13-cis-retinoic acid 4 to 5 fold.

EXPERIMENTAL EXAMPLE 3

A histologic study was conducted on male and female subjects 45 to 60 years of age, with a history of excessive sun exposure and clinical evidence of photodamaged skin, to compare the two retinoids 0.05% 13-cis-retinoic acid in Purpose Cream and 0.05% tretinoin in cream base. Each of the seven subjects received a once daily application for three months of 0.05% 13-cis-retinoic acid in Purpose Cream to one dorsal forearm and 0.05% tretinoin cream to the other dorsal forearm. Following the three month treatment period a 4 millimeter punch biopsy was obtained from the forearms of each subject. The specimens obtained were fixed in formalin and prepared for light microscopy both by paraffin and methacrylate embedding.

The specimens of the forearms were compared in regard to the following histological features.

(1) Thickening of the epidermis.

(2) Correction of epidermal atypia and cytologic abnormalities.

(3) New blood vessels.

(4) Dispersion of melamin pigment.

(5) Decrease in number of horny cells.

(6) Expansion of the sub-epidermal Grenz zone, reflecting new collagen formation.

The results of the histological study are summarized as follows. In five of the seven subjects, histologic changes characteristic of 0.05% retinoic acid were evident on the forearm treated with tretinoin cream. Similar changes were observed in only three of the 0.05% 13-cis-retinoic acid-treated forearms and in each case were of substantially lesser magnitude. The epidermal alterations of the 13-cis-retinoic acid treatment were more noticeable than retinoic acid especially in improvement of cytologic irregularities. The dermis, by contrast, was scarcely altered with the 13-cis-retinoic acid treatment. The results of the study indicate that 0.05% 13-cis-retinoic acid is inferior to 0.05% retinoic acid in correcting photodamage.

EXPERIMENTAL EXAMPLE 4

A histologic study was conducted on male and female subjects 45 to 0 years of age with a history of excessive sun exposure and clinical evidence of photodamaged skin to compare two retinoids, 0.025% 13-cis-retinoic acid in Purpose Cream and 0.05% tretinoin in cream base. Each of the six subjects received a once daily application for three months of the two retinoids, 13-cis-retinoic acid and all-trans retinoic acid, to opposite forearms. The procedures used in this study and the parameters analyzed are identical to those described in Example 3.

The results of the histologic study indicate that all six individuals responded adequately to the 0.05% all-trans retinoic acid with marked thickneing of both the epidermis and the Grenz zone. Equivalent histologic changes were observed in the 0.25% 13-cis-retinoic acid treated specimens. Thus the two treatments were histologically indistinguishable. Therefore, the difference between the two retinoids is merely quantitative in that 13-cis-retinoic acid is less potent than all-trans retinoic acid. The difference between the two retinoids can be overcome by increasing the concentration of 13-cis-retinoic acid to make both compounds biologically equivalent.

From the foregoing embodiments, and the disclosure of my co-pending application incorporated herein by reference it will be seen that the invention has the following advantages inter alia:

A. Clinical

Effacement of fine wrinkles

Smoother surface

Lightens pigmented blotches

Skin has more turgor

Large pores less noticeable

Skin feels livelier

B. Histologic

Thicker epidermis

Normalizes atypia and pre-malignant changes

Atrophy and dysplasia corrected

Stimulates blood flow; new vessels formed

Stimulates fibroblasts with new collagen formation

Increases ground substance

Melanin within keratinocytes is decreased

It will be recognized by those skilled in the art that changes may be made to the above-described embodiments of the invention without departing from the broad inventive concepts thereof. It is understood, therefore, that this invention is not limited to the particular embodiments disclosed, but it is intended to cover all modifications which are within the scope and spirit of the invention as defined by the appended claims.

I claim

1. A method for retarding and reversing the loss of collagen fibers, abnormal changes in elastic fibers, and deterioration of small blood vessels in sundamaged human skin, comprising applying topically to the surface of the skin a composition comprising effective amounts of a retinoid in a nontoxic, dermatologically acceptable vehicle in a program of maintenance therapy, whereby the skin substantially regains and maintains its firmness, turgor and elasticity during said therapy, said composition and amounts of retinoid therein being selected so as to provide a dose for application which is insufficient to cause excessive irritation.

2. A method according to claim 1 wherein said retinoid is selected from the group consisting of retinoic acids, retinoic acid derivatives and stereoisomers thereof.

3. A method according to claim 2 wherein said retinoic acid, retinoic acid derivatives is selected from the group consisting of 13-cis-retinoic acid, 13cis-retinoic acid derivatives and thereof.

4. A method according to claim 1 wherein said retinoid is selected from the group consisting of (E)-4-[4-methyl-6-(2,6,6-trimethyl-1-cyclohexen-1-yl)-] benzoic acid; 4-[(5,6,7,8-tetrahydro-5,5,8,8-tetramethyl-2-naphthalenyl)ethylnyl]-benzoic acid; and (E)-4-[2-(5,6,7,8-tetrahydro-7-hydroxy-5,5,8,8-tetramethyl-2-naphthalenyl-1-propenyl] benzyl alcohol.

5. A method according to claim 1 wherein said retinoid is selected from the group consisting of 13-cis-retinoic acid; (all-E)-9-(4-methoxy-2,3,6-trimethylphenyl)-3,7-dimethyl-2,4,6,8-nonatetraenoic acid ethyl ester; (all-E)-9-(4-methoxy2,3,6,-trimethylphenyl)-3,7-dimethyl-2,4,6,8,-nonatetraenoic acid; N-ethyl-9-(4-methoxy-2,3,6-trimethylphenyl)-3,7-dimethyl2,4,6,8-nonatetraenamide; (E,E)-9-(2,6-dichloro-4-methoxy-3-methylphenyl)-3,7-dimethyl-2,4,6,8-nonatetraenoic acid ethyl ester; 7,8-didehydroretinoic acid; (E,E)-4-[2-methyl-4-(2,6,6-trimethyl-1-cyclohexen-1-yl)-1,3-butadienyl]benzoic acid; (all-E)-3,7-dimethyl-(3-thienyl)-2,4,6,8-nonatetraconic acid; (E,E,E)-3-methyl-7-(5,6,7,8-tetrahydro-5,5,8,8-tetramethyl-2-naphthalenyl)-2,4,6-octatrienoic acid; (E)-6-[2-(2,6,6-trimethyl- 1-cyclohexen-1-yl)ethenyl]-2-naphthalenecarboxylic acid; (E,E,E)-7-(2,3-dihydro-1,1,3,3-tetramethyl-1H-inden-5-yl)-3-methyl-2,4,6-octatrienoic acid; (E)-4-[2-(2,3-dihydro-1,1,3,3-tetramethyl-1H-inden-5-yl)-1-propenyl]benzoic acid; TTNPB (E)-4-[2-(5,6,7,8-tetrahydro-5,5,8,8-tetramethyl-2-naphthalenyl-1propenyl] benzoic acid; (E)-4-[2-(5,6,7,8-tetrahydro-3-methyl-5,5,8,8-tetramethyl-2-naphthalenyl)-1-propenyl]benzoic acid; (E)-1,2,3,4-tetrahydro-1,1,4,4-tetramethyl-6-(1-methyl-2phenylethenyl) naphthalene; 6-(1,2,3,4-tetrahydro-1,1,4,4-tetra-methyl-6-naphthyl)-2-naphthalene-carboxylic acid; [(E)-6-[2-(4-(ethylsulfonyl)phenyl]-1-methylethenyl]-1,2,3,4-tetrahydro-1,2,3,4-tetrahydronaphth-7-yl)-1-[4-tetrazol-5-yl)phenyl]-1-propene] *(E)-2-(1,1,4,4-tetramethyl-1,2,3,4-tetrahydronaphth-7-yl)-1-(4-tetrazol-5-yl)phenyl)-1-propene.*

6. A method according to claim 1 wherein said skin is human facial skin.

7. A method according to claim 2 wherein said skin is human facial skin.

8. A method according to claim 3 wherein said skin is human facial skin.

9. A method according to claim 1 wherein said vehicle is a cream ointment.

10. A method according to claim 1 wherein said vehicle is an emollient vehicle.

11. A method according to claim 1 wherein said retinoid is retinol.

* * * * *